(12) United States Patent
Snow

(10) Patent No.: US 6,177,160 B1
(45) Date of Patent: Jan. 23, 2001

(54) CONTAINER CONTAINING CONTRAST AGENTS

(75) Inventor: Robert Snow, Wayne, PA (US)

(73) Assignee: Nycomed Imaging AS, Oslo (NO)

( * ) Notice: Under 35 U.S.C. 154(b), the term of this patent shall be extended for 0 days.

(21) Appl. No.: 09/258,397

(22) Filed: Feb. 26, 1999

Related U.S. Application Data

(63) Continuation of application No. PCT/GB97/02310, filed on Aug. 27, 1997
(60) Provisional application No. 60/048,052, filed on May 30, 1997.

(30) Foreign Application Priority Data

Aug. 27, 1996 (GB) .................................................. 9617811

(51) Int. Cl.[7] .............................. A61B 10/00; B32B 1/00; B32B 1/04
(52) U.S. Cl. ...................... 428/35.7; 428/36.5; 428/36.8; 428/66.3; 600/458
(58) Field of Search ................................. 428/35.7, 36.5, 428/36.8, 66.3; 600/458

(56) References Cited

U.S. PATENT DOCUMENTS

| 2,573,637 | * | 10/1951 | Bender | 128/272 |
| 4,877,664 | * | 10/1989 | Maeda et al. | 428/35.9 |
| 5,558,854 | * | 9/1996 | Quay | 424/9.52 |
| 5,773,024 | * | 6/1998 | Unger et al. | 424/450 |

FOREIGN PATENT DOCUMENTS

| WO 95/03835 | 2/1995 | (WO) . |
| WO 96/01105 | 1/1996 | (WO) . |

* cited by examiner

*Primary Examiner*—Ellis Robinson
*Assistant Examiner*—Sandra M. Nolan
(74) *Attorney, Agent, or Firm*—Bacon & Thomas

(57) ABSTRACT

Plastics material-containing closed containers (e.g., elastomer-stoppered vials) for contrast agents and contrast agent precursors which incorporate or are adapted to incorporate a volatile substance (e.g., a gaseous halocarbon such as a perfluorocarbon), where the plastics material is pretreated by exposure to the volatile substance. Such containers may enhance the storage stability of the contrast agent or precursor content.

16 Claims, No Drawings

US 6,177,160 B1

CONTAINER CONTAINING CONTRAST AGENTS

RELATED APPLICATIONS

This application is a continuation application of pending international application number PCT/GB97/02310 filed Aug. 27, 1997, of which the entire disclosure of the pending, prior application is hereby incorporated by reference, and claims benefit of provisional application 60/048,052 filed May 30, 1997.

FIELD OF THE INVENTION

This invention relates to storage means for contrast agents, more particularly for contrast agents which incorporate or are adapted to incorporate volatile substances.

BACKGROUND

It is well known that ultrasonic imaging comprises a potentially valuable diagnostic tool, for example in studies of the vascular system, particularly in cardiography, and of tissue microvasculature. A variety of contrast agents has been proposed to enhance the acoustic images so obtained, including suspensions of solid particles, emulsified liquid droplets, gas bubbles and encapsulated gases or liquids. It is generally accepted that low density contrast agents which are easily compressible are particularly efficient in terms of the acoustic backscatter they generate, and considerable interest has therefore been shown in the preparation of gas-containing and gas-generating systems, e.g. to contrast agents which incorporate or are adapted to incorporate volatile substances.

Much attention has been given to the selection of gases for gas-containing ultrasound contrast media in order to enhance properties such as their stability and duration of echogenic effect. Thus, for example, WO-A-9305819 proposes use of free microbubbles of gases having a coefficient Q greater than 5 where $$Q = 4.0 \times 10^{-7} \times \rho / C_s D$$

($\rho$ being the density of the gas in $kg.m^{-3}$, $C_s$ the water solubility of the gas in $moles.l^{-1}$ and D the diffusivity of the gas in solution in $cm^3.sec^{-1}$). An extensive list of gases said to fulfill this requirement is presented, this including a variety of hydrocarbons such as alkanes, alkenes etc. and halogenated compounds such as sulphur hexafluoride, disulphur decafluoride, tungsten hexafluoride, brominated and/or chlorinated and/or fluorinated and/or iodinated hydrocarbons, brominated aldehydes, fluorinated ketones, fluorinated amines, fluorinated mercaptans etc.

EP-A-0554213 suggests that one may impart resistance against collapse under pressure to gas-filled microvesicles by introduction thereto of at least one gas whose solubility in water, expressed in litres of gas/litre of water under standard conditions, divided by the square root of its molecular weight does not exceed 0.003. Gases said to be preferred include halogenated compounds such as sulphur hexafluoride, selenium hexafluoride and various Freons®.

WO-A-9416739 discloses ultrasound contrast agents comprising liquid-in-liquid colloidal dispersions in which the dispersed phase is a liquid having a boiling point below the body temperature of the subject to be imaged. Such agents thus undergo a phase change to an echogenic gaseous foam following administration to the subject. Examples of suitable volatile dispersed phase liquids are said to include aliphatic hydrocarbons such as butanes and pentanes, and organic halides, in particular fluorocarbons such as perfluorobutane, perfluoropentane and perfluoroneopentane.

WO-A-9503835 proposes use of microbubbles containing a gas mixture the composition of which is based on considerations of gas partial pressures both inside and outside the microbubbles, so as to take account of osmotic effects on microbubble size. Representative mixtures comprise a gas having a low vapour pressure and limited solubility in blood or serum (e.g. a fluorocarbon) in combination with another gas which is more rapidly exchanged with gases present in normal blood or serum (e.g. nitrogen, oxygen, carbon dioxide or mixtures thereof).

WO-A-9516467 suggests use of ultrasound contrast media containing a mixture of gases A and B, where gas B is present in an amount of 0.5–41% v/v, has a molecular weight greater than 80 daltons and has aqueous solubility below 0.0283 ml/ml water under standard conditions. Representative gases B include halogenated gases such as sulphur hexafluoride and a variety of brominated and/or chlorinated and/or fluorinated hydrocarbons. Representative gases A, which comprise the balance of the mixture, include air, oxygen, nitrogen, carbon dioxide and mixtures thereof.

WO-A-9608234 claims containers comprising an aqueous lipid suspension phase and a gaseous phase, e.g. comprising a hydrocarbon such as an alkane or alkene or, more preferably, a fluorinated gas such as a perfluorocarbon, which is substantially separate from the lipid phase. Agitation of the contents of such containers is said to produce gas-filled liposome compositions which are useful as contrast agents in, for example, ultrasonic or magnetic resonance imaging.

WO-A-9618420 is directed to products comprising gas bubbles immobilised within a frozen physiologically acceptable aqueous carrier medium containing appropriate stabilising additives etc.; such products may be thawed to generate injectable ultrasound contrast agents. Representative gases are said to include halogen-containing gases such as sulphur hexafluoride, perfluoromethane, perfluoroethane, perfluoroethene, perfluoropropane, perfluoropropene, perfluorobutane, perfluorobut-2-ene, perfluorobutadiene, perfluorocyclobutane, perfluoropentane, perfluorocyclopentane and mixtures thereof.

Contrast agents such as those disclosed in the above-mentioned EP-A-0554213, WO-A-9503835 and WO-A-9516467 are typically intended to be supplied as dry formulations, e.g. comprising appropriate surfactants, additives, stabilisers etc., under an atmosphere of the intended gas content. Such dry formulations may be reconstituted by addition of an appropriate carrier liquid, e.g. sterile pyrogen-free water or saline, prior to administration, e.g. by intravenous injection.

Contrast agents such as those of WO-A-9416739 and WO-A-9608234 will be supplied as liquid formulations. Those of WO-A-9608234 specifically require the presence of gas in the headspace above the aqueous lipid phase. Any headspace above stored forms of contrast agents according to WO-A-9416739 may contain some dispersed phase material in vapour form by virtue of the stated volatility of this material.

In general contrast agents and precursors therefor such as dry formulations will typically be supplied in closed containers, for example in vials or other vessels closed with closure means such as stoppers or septa, or in pre-filled syringes. The contents of such containers may advantageously be such as to constitute or generate an appropriate unit dose of the contrast agent. Containers such as vials may typically comprise glass and/or plastics materials and be closed with closure means comprising plastics materials, for example elastomers. Containers such as syringes may likewise comprise glass and/or plastics material and typically may incorporate plungers comprising plastics material.

SUMMARY AND DESCRIPTION OF THE INVENTION

The present invention is based in part on the finding that where contrast agents comprising a volatile substance are stored in closed containers comprising a plastics material, the storage stability of such agents, e.g. as measured by the length of storage time over which the product remains capable of generating consistently reproducible echogenicity under standardised conditions, may be significantly enhanced by pretreating such plastics material with said volatile substance. Furthermore, it has been found that such pretreated plastics materials may also be employed as sources of volatile substance for introduction into the closed containers and thereby into the contrast agent or precursor therefor contained therein.

Thus according to one aspect of the present invention there is provided a closed container containing a contrast agent or precursor therefor which incorporates or is adapted to incorporate a volatile substance, said container at least in part comprising a plastics material, characterised in that said plastics material is pretreated by exposure to a sample of said volatile substance prior to closure of the container.

Examples of closed containers which may be useful in accordance with the invention include vials, for example of glass, plastics material or glass at least partly lined with plastics material, such vials for example being closed by means of stoppers, septa or screw caps which may comprise plastics material and/or incorporate sealing inserts and/or liners comprising such material; syringes, which may for example be single-chambered, two-chambered or multi-chambered and may for example comprise glass, plastics material or glass at least partly lined with plastics material, such syringes for example incorporating plungers comprising and/or coated with plastics material; and bags, boxes and cases, for example comprising and/or coated with substantially impermeable materials such as metal foils and also including plastics material, such bags, boxes and cases typically containing a plurality of contrast agent-containing vials. If desired, containers such as those described above may additionally or alternatively include inserts comprising plastics material, for example in the form of rods, tubes, spheres, discs, wafers, sponges, foams, aerogels, honeycomb lattices, films and the like. In containers such as syringes the plunger effectively constitutes a form of closure means; further closure means may also be present on, for example, prefitted needles or needle fitting positions.

It will be appreciated that where containers in accordance with the invention incorporate more than one plastics material and/or plastics material component, any or all of these materials and/or components may be pretreated with the volatile substance.

Plastics materials useful in accordance with the invention include a wide range of natural and synthetic polymer materials. Particularly where the materials are used as closure or sealing means such as stoppers, septa, screw caps, cap inserts or syringe plungers it may be advantageous to employ elastomeric polymers, examples of which include but are not limited to polyethylene, polypropylene, polyisobutylene, polystyrene, polyvinylchloride, polyacrylonitrile, perfluorinated polymers such as Teflon®, natural rubber, butyl rubber, synthetic rubbers such as Hycars® or neoprene, silicone polymers, Teflon®-silicone laminates, Teflon®-rubber laminates and other elastomers known in the art to be useful in, for example, closing vials and like vessels containing pharmaceuticals, diagnostic agents etc.

Plastics materials used in accordance with the invention may if desired incorporate absorbants, e.g. inorganic materials such as zeolites or molecular sieves, for example to enhance uptake of the volatile substance during pretreatment.

Furthermore, the size and shape of plastics materials such as stoppers and inserts may be selected to give appropriate properties as regards, for example, the extent of loading of volatile substance during pretreatment and the subsequent rate of release of volatile substance, e.g. where a plastics material is used as a source of volatile substance for introduction into a closed container. Thus dimensions such as thickness may be increased to enhance the amount of volatile substance absorbed or adsorbed. The use of plastics materials having a relatively high surface area:volume ratio, for example materials which are porous, fibrous (e.g. as in fibre bundles) or rod-shaped or have flanged, ribbed, grooved or roughened surfaces, may enhance the rates of both pretreatment uptake and subsequent release of volatile substance.

The volatile substance may in general comprise one or more gases (which term includes any substances, including mixtures, substantially or completely in gaseous, including vapour, form at the normal human body temperature of 37° C.), volatile liquids (e.g. having a boiling point not exceeding 60° C.), solids (e.g. which generate a significant vapour pressure through sublimation or from generation of gas by decomposition) and mixtures of any of the foregoing. Representative volatile substances include low molecular weight hydrocarbons, e.g. containing up to 10 carbon atoms, for example as in butanes, pentanes, hexanes, heptanes and corresponding cycloalkanes, alkenes etc. More preferably, however, the volatile substance is a halogen-containing substance, for example containing at least one halogen atom selected from bromine, chlorine, fluorine and iodine, preferably from chlorine and/or fluorine; the use of fluorinated, more particularly perfluorinated compounds may be especially advantageous. Representative halogen-containing compounds thus include sulphur halides such as sulphur hexafluoride or disulphur decafluoride and organic halides, e.g. aliphatic (which may be straight chain or branched and saturated or unsaturated), cycloaliphatic, araliphatic or aromatic halides containing up to 20 carbons, for example chlorocarbons such as chloroform, methylene chloride or trichloromethane; Freons® such as trichlorofluoromethane, dichlorodifluoromethane, chlorotrifluoromethane, dichlorotetrafluoroethane or chloropentafluoroethane; fluorobromocarbons such as bromoheptadecafluorooctane; iodocarbons such as 1,3,5-triiodobenzene or 1,3,5-tris (trifluoromethyl)-2,4,6-triiodobenzene; halogenated ether anaesthetics such as seroflurane or desflurane; and saturated or unsaturated, aliphatic or cycloaliphatic fluorocarbons, e.g. containing up to 8 carbon atoms, as in fluorinated (preferably perfluorinated) derivatives of alkanes such as methane, ethane, propanes, butanes, pentanes, hexanes, heptanes or octanes; alkenes such as ethylene, propylene, butenes, butadiene or pentenes; alkynes such as acetylene, propyne or butynes; cycloalkanes such as cyclopropane, methylcyclopropane, cyclobutane, cyclopentane or cyclohexane; and arenes such as benzene.

The use of gaseous halogen-containing compounds, e.g. perfluorinated gases such as sulphur hexafluoride, perfluoropropane, perfluorobutane or perfluoropentane, is preferred. Such gases may if desired be admixed with other non-halogenated gases, for example such as air, oxygen, nitrogen, carbon dioxide or mixtures thereof.

Contrast agents present in containers according to the invention may take any appropriate form and include, for example, aqueous compositions adapted to receive and stabilise gas microbubbles, e.g. as described in U.S. Pat. No. 4,466,442 or WO-A-9115244; dispersions in appropriate carrier liquids of gas microbubbles, which may optionally be encapsulated as in gas-filled microballoons (e.g. wherein the gas is contained within enveloping material such as a polymer, protein or film-forming surfactant, as in phospholipid vesicles etc.), volatile liquids or solid microparticles; and solid contrast agent precursor formulations for reconstitution with, for example, a carrier liquid such as sterile water or saline for injection. Such solid formulations may, for example, be prepared by lyophilisation and will typically contain one or more surfactants, e.g. film-forming lipids such as phospholipids, additives, for example cryoprotectants and/or tonicity adjusters, stabilisers etc.

Pretreatment of plastics material for use in or as closed containers in accordance with the invention may be effected by exposure to the substance at, for example, ambient or elevated temperature and pressure, e.g. in a sealed reactor such as a Parr bomb; the conditions may advantageously be such that the material becomes saturated with absorbed or adsorbed volatile substance. Where necessary or desired, an atmosphere comprising the volatile substance may also be filled into the container prior to closing. Alternatively it may be sufficient to allow volatile substance from the pretreated plastics material to permeate into the container and thereby interact with the contrast agent or precursor therefor. This latter procedure may be of advantage as regards processing costs. Thus processes involving introduction of volatile substance into containers such as vials, e.g. by evacuation of one or more vials in a vacuum chamber, for example in the chamber of a lyophilisation apparatus as part of a lyophilisation process, and subsequent introduction to the chamber of volatile substance, may tend to result in wastage of residual volatile substance in the chamber. Pressure treatment of plastics material, on the other hand, may permit more efficient use of residual volatile substance, which may readily be returned to source on completion of the treatment.

After closing of containers such as vials with closure means such as stoppers, septa, screw caps and the like it may be advantageous further to seal the outer surface of the closure, for example with metal foil or a metal crimp cap, or by application of a layer of material which is substantially impermeable to the volatile substance, for example an appropriate natural or synthetic wax or silicone sealant, or a hydrophilic material, e.g. glycerol or a low molecular weight polyethylene glycol, which is a non-solvent for the volatile substance. Alternatively preformed closure means incorporating such impermeable material, e.g. as a coating or integral component, for example on an outer surface or surfaces thereof, may be employed.

The following non-limitative examples serve to illustrate the invention.

EXAMPLE 1

A vial stopper is placed in a sterile Parr bomb maintained at 0° C. Perfluorobutane is added, and the bomb is sealed and heated to 50° C. for 24 hours. The bomb is then cooled to 20° C., and vented to allow gaseous perfluorobutane to escape. The stopper is removed and used to close a vial containing a lyophilised phospholipid liposome contrast agent formulation and a mixture of air and perfluorobutane in the headspace; the stopper is then covered with an aluminium crimp cap. The concentration of perfluorobutane in the vial and the shelf life of the contrast agent composition are both enhanced relative to a comparable vial in which the stopper is not pretreated with perfluorobutane.

EXAMPLE 2

A vial stopper is treated with perfluorobutane as described in Example 1 and used to close a vial containing a lyophilised phospholipid liposome contrast agent formulation and air in the headspace; the stopper is then covered with an aluminium crimp cap. The composition subsequently generates a perfluorobutane-containing microbubble dispersion upon reconstitution with water for injection.

EXAMPLE 3

Vial stoppers are washed, autoclaved and heat treated (121° C., 15 hours) to remove water absorbed during the autoclaving process. The hot vial stoppers are exposed to gaseous perfluorobutane and allowed to cool to ambient temperature in the presence of this gas.

EXAMPLE 4

Unstoppered vials containing a contrast agent precursor are lyophilised in a lyophilisation chamber equipped with a glove box. After lyophilisation perfluorobutane is introduced to the apparatus. Pretreated vial stoppers prepared as in Example 3 are manually applied to the vials by means of the glove box.

EXAMPLE 5

Vials containing a contrast agent precursor are loosely stoppered with pretreated stoppers prepared as in Example 3 and lyophilised in a lyophilisation chamber, whereafter the stoppers are pressed into a closed position. Nitrogen is introduced into the chamber to release the vacuum and the closed vials are removed. Perfluorobutane is found to be gradually released from the stoppers into the headspace of the vials.

What is claimed is:

1. A closed container containing a contrast agent or a contrast agent precursor which incorporates a volatile substance, said container having closure means consisting of an elastomeric polymer, wherein said closure means has been pretreated by exposure to a sample of said volatile substance prior to closure of the container whereby the elastomeric polymer contains an amount of absorbed or adsorbed volatile substance which enhances the stability of the contrast agent or or contrast agent precursor.

2. A closed container as claimed in claim 1 in the form of a vial or syringe.

3. A closed container as claimed in claim 1 wherein said closure means comprises a stopper, septum, screw cap, cap insert or syringe plunger.

4. A closed container as claimed in claim 1 wherein the outer surface of said closure means is provided with a further sealing means.

5. A closed container as claimed in claim 1, wherein the elastomeric polymer is saturated with the absorbed or adsorbed volatile substance.

6. A closed container as claimed in claim 1 wherein the container is a glass vial and the closure means is a stopper.

7. A closed container as claimed in claim 6, wherein said stopper further comprises a coating or as an integral component a material which is substantially impermeable to the volatile substance.

8. A closed container as claimed in claims 1 wherein said volatile substance comprises a sulphur halide or an aliphatic, cycloaliphatic, araliphatic or aromatic halide containing up to 20 carbon atoms.

9. A closed container as claimed in claim 8 wherein said volatile substance comprises sulphur hexafluoride or a perfluorocarbon containing up to 8 carbon atoms.

10. A closed container as claimed in claim 9 wherein said perfluorocarbon is selected from perfluoropropane, perfluorobutane and perfluoropentane.

11. A closed container as claimed in claim 1 containing an aqueous composition adapted to receive and stabilise gas microbubbles, a dispersion of optionally encapsulated gas microbubbles in a carrier liquid or a solid contrast agent precursor formulation adapted for reconstitution with a carrier liquid.

12. A closed container as claimed in claim 11 wherein said solid contrast agent precursor formulation comprises a lyophilised phospholipid.

13. A closed container as claimed in claim 4 wherein said further sealing means comprises metal foil or a metal crimp cap.

14. A process for the manufacture of a closed container as defined in claim 1 which comprises treating said closure means by exposure to a sample of said volatile substance and thereafter closing said container.

15. A process as claimed in claim 14 wherein said closure means is exposed to said volatile substance at elevated pressure and/or elevated temperature.

16. A process as claimed in claim 14 wherein said closure means is saturated with said volatile substance.

* * * * *